(12) United States Patent
Hancock et al.

(10) Patent No.: US 11,622,671 B2
(45) Date of Patent: Apr. 11, 2023

(54) CONTROL DEVICE FOR A SURGICAL INSTRUMENT

(71) Applicant: CREO MEDICAL LIMITED, Chepstow (GB)

(72) Inventors: Christopher Paul Hancock, Bath (GB); George Ullrich, Bangor (GB); David Webb, Bangor (GB); Louis Turner, Chepstow (GB)

(73) Assignee: CREO MEDICAL LIMITED, Chepstow (GB)

( * ) Notice: Subject to any disclaimer, the term of this patent is extended or adjusted under 35 U.S.C. 154(b) by 923 days.

(21) Appl. No.: 16/074,360

(22) PCT Filed: May 16, 2017

(86) PCT No.: PCT/EP2017/061742
§ 371 (c)(1),
(2) Date: Jul. 31, 2018

(87) PCT Pub. No.: WO2017/198673
PCT Pub. Date: Nov. 23, 2017

(65) Prior Publication Data
US 2019/0167077 A1 Jun. 6, 2019

(30) Foreign Application Priority Data
May 17, 2016 (GB) .................................. 1608634

(51) Int. Cl.
*A61B 1/00* (2006.01)
*A61B 1/018* (2006.01)
(Continued)

(52) U.S. Cl.
CPC ...... *A61B 1/00133* (2013.01); *A61B 1/00066* (2013.01); *A61B 1/00087* (2013.01);
(Continued)

(58) Field of Classification Search
CPC ............ A61B 1/00133; A61B 1/00066; A61B 1/00087; A61B 1/018; A61B 17/29;
(Continued)

(56) References Cited

U.S. PATENT DOCUMENTS 5,993,467 A * 11/1999 Yoon .................. A61B 17/0469
606/147
6,723,106 B1 * 4/2004 Charles .................. B25J 9/1065
606/130

(Continued)

FOREIGN PATENT DOCUMENTS

EP 2 446 834 A1 5/2012
JP H11-326783 A 11/1999
(Continued)

OTHER PUBLICATIONS

British Search Report dated Nov. 17, 2016 issued in British Application No. GB1608634.0.
(Continued)

*Primary Examiner* — Timothy J Neal
*Assistant Examiner* — William B Chou
(74) *Attorney, Agent, or Firm* — ArentFox Schiff LLP

(57) ABSTRACT

A movement transfer mechanism for a surgical scoping device, wherein a rotational proximal input force is transformed into a longitudinal force that is conveyed down the length of an instrument channel of the scoping device, where it is transformed again into an operational movement of a distal instrument. The operational movement can be rotational movement, but may be any movement that changes the orientation or configuration of the distal instrument. By conveying a linear force along the instrument channel rather than a twisting force, the problems of slipping and discon-
(Continued)

tinuous operation of the distal instrument due to friction between the instrument and the instrument channel can be reduced or eliminated.

23 Claims, 5 Drawing Sheets

(51) Int. Cl.
| | |
|---|---|
| *A61B 18/14* | (2006.01) |
| *F16C 1/10* | (2006.01) |
| *A61B 17/29* | (2006.01) |
| *A61B 17/34* | (2006.01) |
| *A61B 18/18* | (2006.01) |
| *F16H 25/20* | (2006.01) |
| *G02B 23/24* | (2006.01) |
| *A61B 18/00* | (2006.01) |

(52) U.S. Cl.
CPC .............. *A61B 1/018* (2013.01); *A61B 17/29* (2013.01); *A61B 17/3478* (2013.01); *A61B 18/1492* (2013.01); *A61B 18/1815* (2013.01); *F16C 1/10* (2013.01); *F16H 25/20* (2013.01); *A61B 18/1442* (2013.01); *A61B 2018/00589* (2013.01); *A61B 2018/00601* (2013.01); *A61B 2018/00607* (2013.01); *A61B 2018/00982* (2013.01); *A61B 2018/141* (2013.01); *A61B 2018/1425* (2013.01); *A61B 2018/1861* (2013.01); *F16C 2316/10* (2013.01); *F16H 2025/2028* (2013.01); *G02B 23/2476* (2013.01)

(58) Field of Classification Search
CPC ............ A61B 17/3478; A61B 18/1492; A61B 18/1815; A61B 18/1442; A61B 2018/00589; A61B 2018/00601; A61B 2018/00607; A61B 2018/00982; A61B 2018/141; A61B 2018/1425; A61B 2018/1861; F16C 1/10; F16C 2316/10; F16H 25/20; F16H 2025/2028; G02B 23/2476
See application file for complete search history.

(56) References Cited

U.S. PATENT DOCUMENTS

| | | | | |
|---|---|---|---|---|
| 8,221,306 | B2* | 7/2012 | Okada | A61B 17/3421 600/129 |
| 10,820,923 | B2* | 11/2020 | Govari | A61B 1/0058 |
| 2002/0010485 | A1 | 1/2002 | Griego et al. | |
| 2005/0192532 | A1* | 9/2005 | Kucklick | A61M 1/0084 604/96.01 |
| 2006/0282117 | A1 | 12/2006 | Berberich et al. | |
| 2008/0249552 | A1* | 10/2008 | Eliachar | A61B 17/320725 606/171 |
| 2009/0163943 | A1* | 6/2009 | Cavanaugh | A61B 17/30 606/180 |
| 2009/0182314 | A1* | 7/2009 | Eliachar | A61B 18/24 606/15 |
| 2009/0270796 | A1* | 10/2009 | Perry | A61M 3/0279 604/35 |
| 2010/0063353 | A1* | 3/2010 | Eliachar | A61B 17/32056 600/106 |
| 2011/0276049 | A1 | 11/2011 | Gerhardt | |
| 2012/0104071 | A1* | 5/2012 | Bryant | A61B 17/068 227/175.1 |
| 2013/0018361 | A1* | 1/2013 | Bryant | A61B 17/07207 606/1 |
| 2013/0324978 | A1* | 12/2013 | Nicholas | F16H 25/20 606/1 |
| 2014/0276722 | A1* | 9/2014 | Parihar | A61B 18/1482 606/33 |
| 2015/0012021 | A1* | 1/2015 | Mihara | A61B 1/018 606/1 |
| 2015/0272603 | A1* | 10/2015 | Shelton, IV | A61B 17/2909 606/207 |
| 2015/0327850 | A1 | 11/2015 | Kostrzewski | |
| 2015/0351747 | A1* | 12/2015 | Martin | A61B 17/0469 606/145 |
| 2016/0135810 | A1* | 5/2016 | Bryant | A61B 17/072 227/176.1 |
| 2016/0175027 | A1* | 6/2016 | Rupp | A61B 18/1445 606/48 |
| 2016/0302817 | A1* | 10/2016 | Worrell | A61N 7/00 |
| 2019/0008541 | A1* | 1/2019 | Norton | A61B 18/1445 |
| 2022/0022735 | A1* | 1/2022 | Agrawal | A61B 1/00057 |

FOREIGN PATENT DOCUMENTS

| | | |
|---|---|---|
| WO | WO 99/05972 A1 | 2/1999 |
| WO | WO 2007/000754 A2 | 1/2007 |
| WO | WO 2014/006369 A1 | 1/2014 |

OTHER PUBLICATIONS

International Search Report and: Written Opinion dated Jul. 11, 2017 issued in International Application No. PCT/EP2017/061742.

* cited by examiner

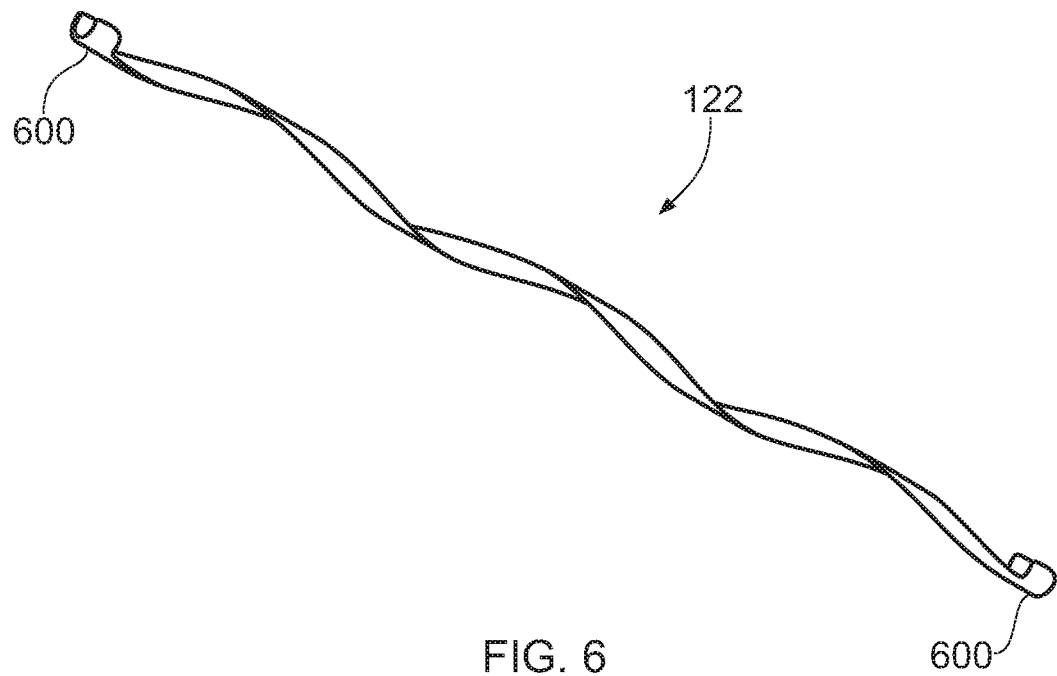
FIG. 6
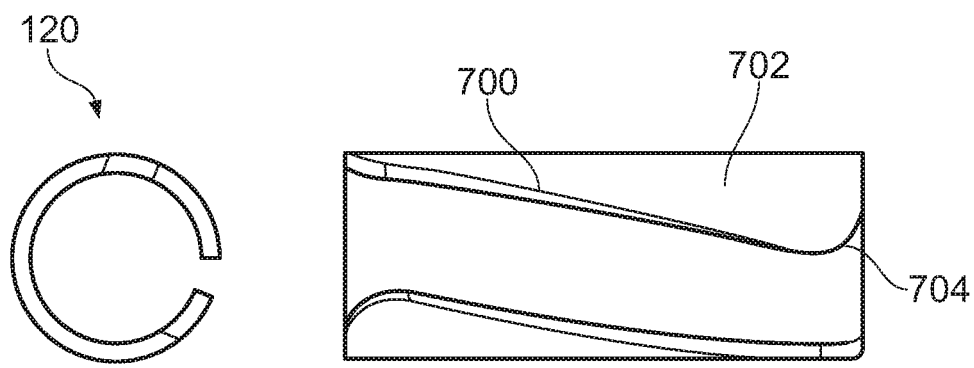
FIG. 7A
FIG. 7B

CONTROL DEVICE FOR A SURGICAL INSTRUMENT

CROSS-REFERENCE TO RELATED APPLICATION

This application is a 35 U.S.C. § 371 National Phase of PCT Application No. PCT/EP2017/061742 filed May 16, 2017, which claims priority to British Application No. GB 1608634.0 filed May 17, 2016. The disclosures of these prior applications are hereby incorporated by reference herein.

FIELD OF THE INVENTION

The present invention relates to a device for controlling movement of a surgical instrument located at the distal end of an instrument channel formed through an instrument cord of a surgical scoping device, such as an endoscope, gastroscope or the like. In particular, the invention relates to a device that enables a rotation force applied by an operator at the proximal end of the instrument channel to be transferred into an operational movement (e.g. rotation) of the surgical instrument at the distal end of the instrument channel.

BACKGROUND TO THE INVENTION

It is common for endoscopes to be provided with surgical instruments at a distal end so surgical procedures can be carried out inside the body in a minimally invasive way. In such procedures, it is important that the operator of the endoscope, for example a surgeon or assistant, has control over the tool at the distal end.

However, this can present a technical challenge as the tool must be controlled via a cable passed down a narrow instrument channel and so it can be difficult to have full control of the surgical instrument. In particular, rotation of the instrument presents a challenge due to friction between the instrument cable and the walls of the instrument channel. When the operator rotates the instrument cable at the proximal end of the instrument channel, this friction causes the instrument to rotate with a jerky, discontinuous motion. This effect is amplified where the endoscope is flexed to go around corners, which can be necessary to get to a surgery site inside the body.

Jerky, discontinuous motion leaves the operator without full control of the surgical instrument and in particular makes small movement of the instrument unpredictable. As a result it can be difficult to use surgical instruments that do not have rotational symmetry in a scoping device environment, because it is difficult accurately to control the orientation of the instrument independently of the surgical scoping device. Indeed, in conventional procedures, the orientation of the instrument may be controlled by rotating the entire instrument cord of the scoping device, which can be unwieldy.

SUMMARY OF THE INVENTION

At its most general, the present invention proposes a movement transfer mechanism in which a rotational proximal input force is transformed into a longitudinal force that is conveyed down the length of the instrument channel, where it is transformed again into an operational movement of a distal instrument. The operational movement is preferably rotational movement of the distal instrument, but may be any movement that changes the orientation or configuration of the distal instrument. For example, the operational movement may be opening the jaws of a forceps instrument, or retracting a surgical snare, or similar.

By conveying a longitudinal (i.e. linear) force along the instrument channel rather than a twisting force (torque), the problems of slipping and discontinuous operation (e.g. rotation) of the distal instrument due to friction between the instrument and the endoscope instrument channel can be reduced or eliminated.

According to one aspect of the invention there is provided an instrument rotation mechanism for a surgical scoping device, the instrument rotation mechanism comprising: a housing mountable at a proximal end of an instrument channel of a surgical scoping device; a proximal actuator mounted to rotate relative to the housing; an elongate force transfer element configured to be slidably mounted within and to extend along the instrument channel of a surgical scoping device; a proximal coupler operably engaged with the proximal actuator and elongate force transfer element to transform rotational movement of the proximal actuator relative to the housing into linear movement of the elongate force transfer element relative to the instrument channel; a distal end effector that is securable to a distal portion of a surgical instrument mounted in the instrument channel; and a distal coupler operably engaged with the distal end effector and elongate force transfer element to transform linear movement of the elongate force transfer element relative to the instrument channel into an operational movement for the surgical instrument. Preferably the operational movement comprises rotational movement of the distal end effector relative to the instrument channel. By converting longitudinal (i.e. axial motion) of the elongate force transfer element (which is sometimes referred to herein as a follower) into rotational motion at the distal end of the instrument channel rather than transmitting rotational motion along the whole length of the instrument channel, rotational motion of the instrument can be made smoother and less jerky thereby giving a user greater control of the instrument. In addition, as the input motion at a proximal end of the instrument channel is rotational, the device can be intuitive and easy to use.

The proximal coupler may be slidably mounted in the housing. The housing may include a rotation constraining element arranged to prevent the elongate force transfer element from rotating relative to the housing, e.g. by engaging the proximal coupler in a manner that prevents it from rotating relative to the housing. For example, the rotation constraining element may define a linear sliding track for the proximal coupler, wherein the sliding track is fixed relative to the housing. The elongate force transfer may be similarly constrained. For example, it may have a proximal engagement feature that is coupled to the sliding track. The rotation constraining element may be formed by a guide member that is mounted in the housing. The guide member may be configured to sit inside an interior cavity formed by the proximal actuator. For example, the proximal actuator may be a tube mounted to the housing, and the guide member may be mounted in the tube and secured to the housing in a non-rotatable manner at its proximal end.

The proximal coupler and proximal actuator may be operably connected via a non-locking thread-type engagement. In this context, non-locking means that the angle or pitch of the thread is such that a component of an applied axial force along the thread can overcome an opposing frictional force to cause a relative rotational movement. In one example, the term thread-type engagement may mean a helical path formed on one component that is engaged by the other component in a manner that means relative movement between the two components is constrained to occur in a helical manner. Both components may have cooperating helical formations. Alternatively, one component may have a helical formation and the other may have an engagement feature that tracks the helical formation.

In one example, the proximal actuator may comprise a helical formation and the proximal coupler comprises an engagement element mounted on and movable along the helical formation. The helical formation may comprise a recessed track and the engagement element may be a pin that sits in the recessed track. In another example, the helical formation may be a raised track and the engagement element may be a runner mounted on the track. In yet another example, the helical formation may be on the proximal coupler and the engagement element may be on the proximal actuator.

A similar configuration may be adopted at the distal end, i.e. the distal coupler and distal end effector may be operably connected via a non-locking thread-type engagement, e.g. of the type described above.

In one example, the distal end effector comprises a helical formation and the distal coupler comprises an engagement element mounted on and movable along the helical formation. The helical formation may be a helical sleeve mounted around the distal portion of the surgical instrument, and the engagement element may comprise a ring having a helical portion that cooperates with the helical sleeve.

The mechanism may be configured such that there is a one-to-one correspondence between rotational motion of the proximal actuator and rotational motion of the instrument about its longitudinal axis. The couplings at the proximal and distal end may be geared to take account of minor material deformation (i.e. stretch or compression) in the elongate force transfer element. This gearing may manifest itself as a difference in pitch between a first helical formation at the proximal end and a pitch of a second helical formation at the distal end. For example, the pitch of the first helical formation may be greater than, e.g. equal to or greater than 1.5 times greater than, the pitch of the second helical formation.

A longer pitch in a helical thread means that less torque is needed to convert rotational to axial motion (e.g. at the proximal end of the instrument channel), or, at the distal end of the instrument channel, a longer pitch means that less torque is produced by axial motion of the elongate force transfer element.

In addition, a longer pitch means that the elongate force transfer element needs to be moved a greater distance to turn the instrument through a given angle.

However, an advantage of a long pitch is that it reduces the effect any stretch or compression in the elongate force transfer element has on the required amount of rotation input by the user and/or on the output rotation of the instrument.

By gearing the couplings at the proximal and distal ends as discussed above, a balance can be struck between these issues. Where thread-like couplings (e.g. helical formations) are used, the pitches of the threads may be selected so that they are non-locking at both the proximal and distal ends, and that the pitch at the proximal end is greater than the pitch at the distal end.

In one example, the distal end effector is a helical sleeve and the distal coupling member is a ring having a helical cut-out section configured to engage with the distal helical sleeve. The ring may be a rigid element, e.g. laser cut from a suitable material (e.g. a stainless steel tube or the like). The ring can be secured to the elongate force transfer element by any suitable means, e.g. interference fit, adhesive or the like.

The ring may comprise a number of inwardly directed projections to facilitate a grip between the ring and the elongate force transfer element. This can ensure that axial motion of the elongate force transfer element is efficiently converted to rotational motion of the instrument by preventing the ring from slipping along the elongate force transfer element or rotating about its longitudinal axis.

In an alternative embodiment, the distal end effector may be a sleeve having a pin protruding from an outer surface, and the distal coupling member may be a tube having a helix recessed into an inner surface.

The rotation mechanism may comprise an instrument cable that extends through the instrument channel for connection to the surgical instrument, wherein the proximal actuator is secured to a proximal portion of the instrument cable. All components of the rotation mechanism may comprise a longitudinal passage therethrough for conveying the instrument cable. The elongate force transfer element may comprise a tubular element having a longitudinal passage or lumen for conveying the instrument cable runs along the interior of the elongate force transfer element.

The instrument cable may have a lubrication coating to reduce friction between the instrument cable and the instrument channel walls. In one embodiment, the instrument cable may be a coaxial transmission line, and the instrument may be an electrosurgical instrument configured to deliver radiofrequency and/or microwave frequency energy. The coaxial transmission line may be encased in a sleeve suitable for insertion through the instrument channel. The coaxial transmission line may extend between a proximal end, e.g. having a microwave connector for connecting to a suitable radiofrequency and/or microwave signal generator, and a distal end at which the instrument is located. The length of the coaxial transmission line may be suitable for endoscopic procedures, for example 2000 mm or more.

By providing a coaxial transmission line as the instrument cable, and an electrosurgical instrument configured to deliver radiofrequency and/or microwave frequency energy, the instrument may be used for cutting tissue and/or haemostasis (i.e. promoting blood coagulation).

The instrument cable may be used to assist rotation of the instrument because it rotates with the proximal actuator. The distal end effector may thus be secured to a distal portion of the instrument cable. For example, the distal end effector may comprise a helical sleeve arranged to fit over the instrument cable. The helical sleeve may have an end clip at each end of the sleeve to grip the instrument cable such that axial motion of the distal coupling member results in rotation of the instrument cable. In this configuration, the instrument cable may thus be rotated at both the proximal end and distal end of the instrument channel. This ensures that torque is distributed along the length of the instrument cable.

As mentioned above, the conversion of the axial motion of the elongate force transfer element into rotational motion may not be 100% efficient. This may also arise because the instrument cable is not anchored at the distal end of the instrument channel. The "lost" movement in this scenario may be more noticeable when 'pushing' the elongate force transfer element (i.e. sliding it in a distal direction).

To reduce or eliminate this lost movement, the instrument cable may be pre-twisted between the proximal and distal portions to facilitate rotation in a pre-determined direction. In other words, the instrument cable may be arranged to naturally urge the distal portion to rotate in a certain sense relative to the proximal actuator. This sense preferably corresponds to the rotation caused by moving the elongate force transfer element in a distal direction.

By pre-tensioning the instrument cable as described above, conversion of axial to rotational motion at the distal end of the instrument channel may be made more efficient. Pre-tensioning may also help to achieve one-to-one correspondence between rotational motion at the proximal end of the instrument channel and rotational motion of the instrument about its longitudinal axis.

The elongate force transfer element may comprise a proximal portion and a distal portion, wherein the instrument rotation mechanism further comprises: an intermediate rotatable member located between the proximal portion and distal portion of the elongate force transfer element, a proximal intermediate coupler operably engaged with the intermediate rotatable member and the proximal portion of the elongate force transfer element to transform linear movement of the proximal portion of the elongate force transfer element relative to the instrument channel into rotational movement of the intermediate rotatable member relative to the instrument channel, and a distal intermediate coupler operably engaged with the intermediate rotatable member and the distal portion of the elongate force transfer element to transform rotational movement of the intermediate rotatable member relative to the instrument channel into linear movement of the distal portion of the elongate force transfer element relative to the instrument channel. Thus there is an linear-rotation-linear conversion at an intermediate location on the elongate force transfer element. There may be a plurality of such conversions along the length of the elongate force transfer element. Thus may facilitate distribution of torque along the length of the instrument cable.

The distribution of torque along the instrument cable helps to ensure smooth rotation of the instrument and reduces jerky or discontinuous rotation due to friction of the instrument cable with the inner surface of the instrument channel.

The intermediate rotatable member may comprise a helical sleeve, and the proximal intermediate coupler and the distal intermediate coupler may each comprise a ring having a helical cut-out section configured to cooperate with the helical sleeve. The intermediate helical sleeve may fit over the instrument cable and may have an end clip at each end of the sleeve to grip the instrument cable such that axial motion of the proximal intermediate coupler results in rotation of the instrument cable.

Alternatively, the intermediate rotatable member may be a sleeve having a pin protruding from an outer surface, and each intermediate coupler may be a tube having a helix recessed into an inner surface. In this embodiment, the intermediate sleeve may fit over the instrument cable and may comprise an end clip at each end of the intermediate sleeve to grip the instrument cable such that axial motion of the proximal intermediate coupler results in rotation of the instrument cable.

The housing may be part of a handle for operating the surgical scoping device.

The instrument channel may be arranged to transport fluid to and/or from the instrument. For example, the surgical scoping device may be arranged to deliver or remove fluid from a treatment site. The elongate force transfer element may comprise a plurality of through holes to permit or facilitate passage of fluid along the instrument channel. The elongate force transfer element occupies space in the instrument channel, and therefore can restrict the volume available for fluid. Making the elongate force transfer element porous, e.g. by providing a plurality of holes therethrough, facilitates the passage of fluid. The holes may be dimensioned and positioned in a manner that does not affect the structural rigidity (especially in the longitudinal sense) of the elongate force transfer element. The holes may be formed only in a distal portion of the elongate force transfer element, e.g. in a region where the distal coupling member and distal end effector are also occupies space in the instrument channel.

In some embodiments, the instrument may comprise a needle. For example the needle may be provided for injecting saline, or another liquid, at the distal end of the fluid channel. In certain embodiments, the handle comprises a needle push configured to extend the needle from within a recess in the instrument. In this way, the needle can be hidden within the instrument until it is required by a user. Preferably, the instrument channel comprises a saline channel to allow saline to be pumped from the proximal end to the distal end of the instrument channel, for example to be pumped through the needle.

The elongate force transfer element may be any of: a plastic extruded catheter, a laser cut tube, a tube formed of encapsulated braiding. For example, the elongate force transfer element can be manufactured from PEEK, polyimide, or stainless steel.

The elongate force transfer element may be torque stable such that it is resistant to torsion. This ensures that rotational motion at the proximal end of the instrument channel is efficiently converted to axial motion of the elongate force transfer element, and that axial motion of the elongate force transfer element is efficiently converted back into rotational motion at the distal end of the instrument channel.

BRIEF DESCRIPTION OF THE DRAWINGS

Embodiments of the invention are described in detail below with reference to the accompanying drawings, in which:

FIG. 6 shows a perspective view of the distal rotatable member shown in FIG. 1;

FIGS. 7A and 7B show an end view and a magnified view, respectively, of the distal coupling member shown in FIG. 1;

DETAILED DESCRIPTION; FURTHER OPTIONS AND PREFERENCES

Figure 1:
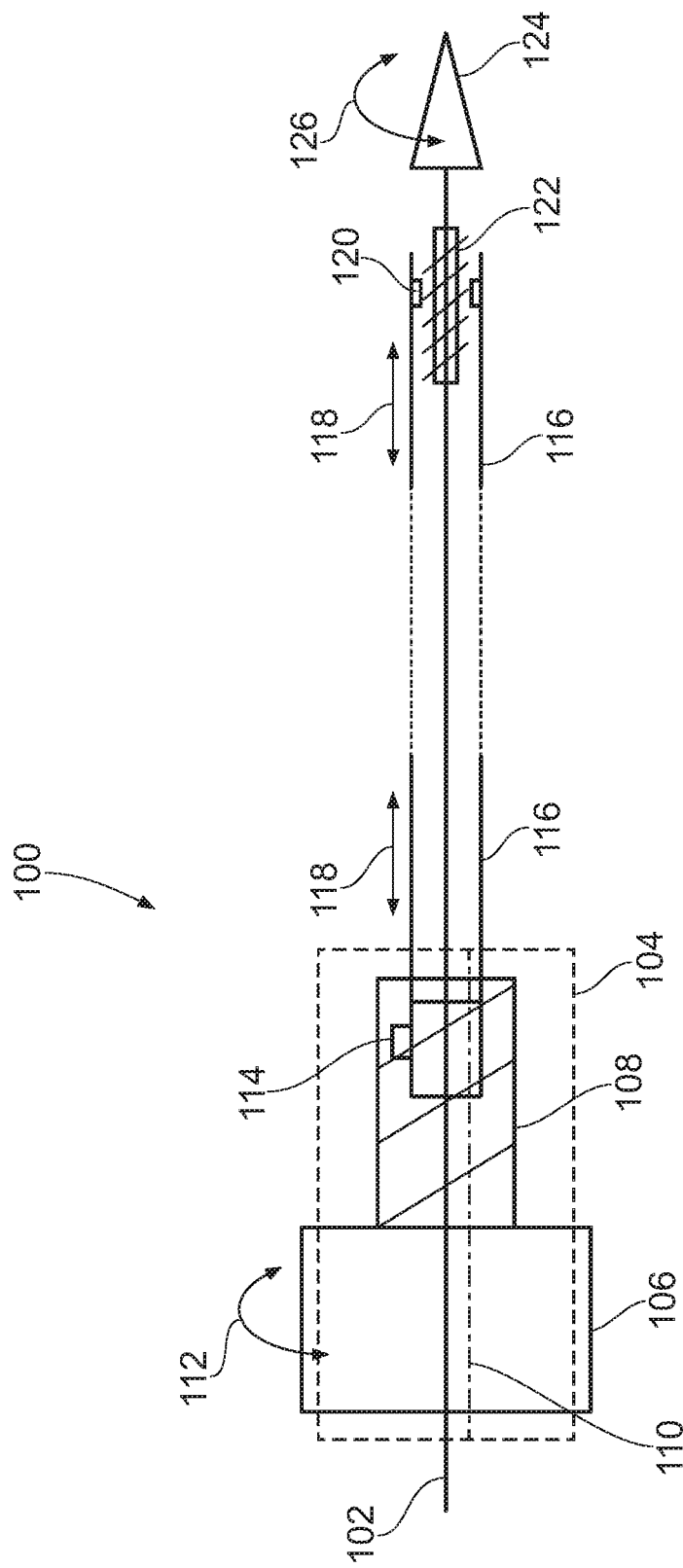
FIG. 1 shows a schematic illustration of a rotation mechanism that is an embodiment of the present invention.

Where features of the embodiments described below are equivalent, the same reference numerals are used and detailed description thereof is not repeated.

A schematic illustration of a rotation mechanism 100 that is an embodiment of the present invention is shown in FIG. 1. The rotation mechanism is intended for using with a surgical scoping device, such as an endoscope. Such devices typically comprises a main body that has an elongate flexible instrument cord extending therefrom. The instrument cord is insertable into the human body, and can be steerable e.g. via controls mounted in or on the body. The instrument cord comprises a plurality of longitudinal passages or lumens therein. One of these passages may be an instrument channel for conveying an instrument to a treatment site. Other lumens may be used for optics and/or for delivering fluid or suction to the treatment site.

The rotation mechanism of the invention is intended for use with an instrument mounted in the instrument channel of the surgical scoping device. The rotation mechanism provides a means of transferring a rotational input motion delivered by an operator at the proximal end (e.g. at the body of the surgical scoping device) into a rotational output motion of the instrument at the distal end of the instrument channel. The instrument may be any device whose orientation relative to a treatment surface is desirably controlled. For example, the instrument may be any one of a snare, forceps, scissors, and energy applicator (e.g. having planar structure as disclosed in WO 2014/006369).

The rotation mechanism 100 illustrated in FIG. 1 comprises an instrument cable 102 that is capable of passing along an instrument channel of a surgical scoping device, and which has an instrument 124 at its distal end. The instrument cable 102 may be a coaxial transmission line configured to transmit radiofrequency (RF) and/or microwave frequency energy through the assembly to an instrument 124. For example, the instrument may be capable of delivering radiofrequency energy for cutting tissue and/or microwave frequency energy for haemostasis (i.e. promoting blood coagulation). A suitable instrument is disclosed in WO 2014/006369.

Figures 3A, 3B:
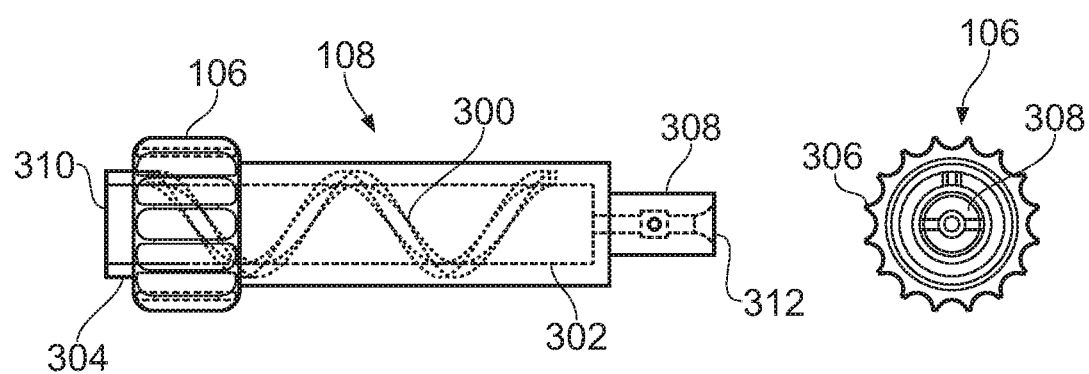
FIGS. 3A and 3B show a side view and an end view of an actuator and rotatable member suitable for use in the rotation mechanism shown in FIG. 1.

The rotation mechanism 100 further comprises, at a proximal end, a casing 104, shown by a dashed line for clarity. In use, the casing is positioned outside of a patient's body and may form part of the body of the surgical scoping device. The casing 104 houses an actuator 106, a rotatable member 108 which is connected to and operable by the actuator 106, and a guide 110. In the embodiment depicted, the rotatable member 108 is a tube comprising a helical channel which is recessed into the inner surface of the tube as shown in FIG. 3A, and so may be referred to below as a threaded tube.

The actuator 106 is configured to at least partially project outside of the casing 104 such that it is able to be manipulated by a user, who may be a surgeon or an assistant. In particular it is configured to be rotated about its longitudinal axis in a clockwise or anti-clockwise direction, as shown by arrow 112. Rotation of the actuator 106 rotates the rotatable member 108 in a corresponding clockwise or anti-clockwise direction. The actuator 106 and rotatable member 108 may be an assembly or may be formed as a unitary component.

A longitudinal passage for receiving the instrument cable 102 runs along the central longitudinal axis of the actuator 106 and the rotatable member 108.

A guide 110 is positioned within the rotatable member 108 and the actuator 106 in the instrument channel, and engages the casing 104 at its proximal end such that it is held in a fixed position and does not rotate with the actuator 106 and rotatable member 108. A coupling member 114 is disposed on the guide 110 such that the coupling member 114 is slidable on the guide 110 in an axial direction. The coupling member 114 is disposed on and constrained by the guide 110 so that it is unable to rotate with the actuator 106 and rotatable member 108.

Coupling member 114 comprises a pin which is configured to engage with the helical channel recessed into the inner surface of the rotatable member 108. When rotatable member 108 is rotated due to manipulation of actuator 106 by a user, the coupling member 114 is engaged by the helical channel recessed into the inner surface of the rotatable member 108 and is moved axially along the guide 110, which provides a linear track along which the coupling member 114 moves without rotation. A pitch of the helical channel is chosen to ensure that the force (torque) required to move the coupling member 114 is not too great.

An elongate force transfer element (referred to below as a follower 116) is connected to coupling member 114 such that axial movement of the coupling member 114 causes axial movement of the follower 116 in either a proximal or distal direction as shown by arrow 118. In one embodiment, the follower 116 is 2 m in length. The follower 116 is hollow, having a central bore or lumen extending along its length, centred on a centre of the follower 116. The instrument cable 102 passes through the bore. The follower 116 may be a catheter manufactured from plastic through an extrusion process to the required. The follower 116 is torque stable, i.e. resistant to torsion. This is to ensure that linear movement of the follower 116 is efficiently converted to rotation of a distal rotatable member 122, as described below. Follower 116 may be manufactured from PEEK (polyether ether ketone), or polyimide.

The instrument cable 102 is preferably fixed in an axial position relative to the casing 104 to assist relative movement of the follower. In one embodiment, the instrument cable 102 is attached to the rotatable member 108 such that rotation of the actuator 106 rotates instrument cable 102 about its longitudinal axis. Thus, the cable is rotated at its proximal end to prevent the introduction of unwanted torsion along the length of the cable.

At the distal end of the follower 116 there is a distal coupling member 120. The distal coupling member 120 is a tubular element as shown in further detail in FIG. 7. The distal coupling member 120 is attached, for example with adhesive, to an inner surface of the follower 116 such that it moves in an axial direction 118 with the follower 116 in response to rotation of actuator 106 as described above.

The distal coupling member 120 is configured to engage with a helical thread on distal rotatable member 122. The distal rotatable member 122 may be a helical sleeve, as shown in FIG. 6, which is fitted over the instrument cable 102, e.g. at a distance of 100 mm from the distal end thereof. This ensures that the distal end of the instrument cable 102 is able to bend freely. The distal coupling member 120 cooperates with the helical thread of distal rotatable member 122 such that axial movement of the follower 116 is converted into rotational movement of distal rotatable member 122 and instrument cable 102 about its longitudinal axis. Rotation of instrument cable 102 rotates surgical instrument 124 in a direction shown by arrow 126.

A user, such as a surgeon or an assistant, is therefore able to control rotation of a surgical instrument 124 at the distal end of an endoscope 100 by rotation of actuator 106 contained within a casing 104 at the proximal end of the endoscope. The rotation of actuator 106 is converted into axial motion of the follower 116 by the rotatable member 108 and coupling member 114. At the distal end of the endoscope 100, the axial motion of the follower 116 is converted back into rotational motion by the distal coupling member 120 and the distal rotatable member 122, thereby rotating the instrument 124 about its longitudinal axis.

Figure 2:
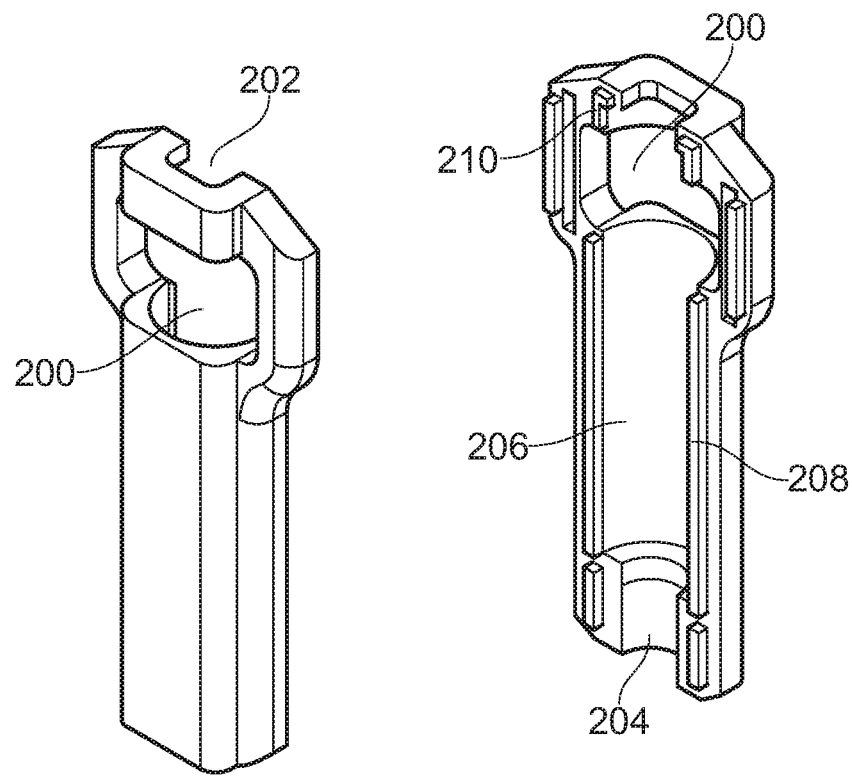
FIG. 2 shows an exploded view of a casing suitable for use with the rotation mechanism shown in FIG. 1.

FIG. 2 shows an exploded view of casing 104. Casing 104 houses actuator 106, rotatable member 108, guide 110 and coupling member 114, as shown schematically in FIG. 1. Although not shown, the casing 104 may form part of a handle of an endoscope.

Casing 104 is formed from two halves for easy assembly. Each half extends from a first end to a second end and has a window 200 towards the first end such that actuator 106 is able to protrude at least partially outside of casing 104 so that it can be manipulated by a user. First and second end faces have openings 202 and 204, respectively, which allow instrument cable 102 to pass through the casing 104.

Each half of the casing 104 has a hollowed out interior section 206 which extends from window 200 towards the second end, such that when the two halves of the casing are brought together the interior section 206 holds rotatable member 108. In the depicted embodiment, rotatable member 108 is a tube comprising a helical channel recessed into the inner surface of the tube. The rotatable member 108 is held by the casing 104 such that it is able to rotate about its longitudinal axis in response to rotation of actuator 106 by a user, but the fit between the casing 104 and the rotatable member 108 should be close such that axial or lateral movement of the rotatable member 108 is minimised. Opening 204 is configured to receive a portion of the rotatable member 108 to minimise unwanted relative movement between the parts.

The first end of casing 104 further comprises a flange 210 which is configured to receive a portion of the actuator 106 and/or rotatable member 108, and is shaped to receive a section of guide 110 as described below. The actuator 106 and rotatable member 108 are thus rotatably mounted inside the housing 104. A portion of the guide 110 is positioned between an interior surface of casing 104 proximate the first end such that when the two halves of the casing 104 are brought together, the casing 104 and actuator 106 clamp the guide 110 in place so that the guide 110 is fixed and does not rotate when the actuator 106 is manipulated by a user. Axial movement of the guide 110 is also prevented to ensure maximum relative movement between the coupling member 114 and the guide 110.

One half of the casing 104 comprises a number of peripheral tongues 208 which are configured to engage with corresponding grooves (not shown) on the opposing half of the casing 104 such that when the two halves are brought together there is an interference fit between the tongues 208 and grooves which attaches the two halves together to stabilise the assembly and prevent lateral relative movement between the two halves.

FIGS. 3A and 3B show a side view (FIG. 3A) and an end view (FIG. 3B) of the actuator 106 and rotatable member 108, which are housed inside casing 104 in use.

The actuator 106 and rotatable member 108 may be formed as a unitary piece or the actuator 106 and rotatable member 108 may be manufactured separately and assembled to form a single component. For example, the rotatable member 108 may be manufactured as a single piece with a stepped outer profile and the actuator 106 may be manufactured as a ring which is slid onto the end of rotatable member 108, with the step in the outer profile of rotatable member 108 holding the actuator 106 in position. Alternative constructions may be used in accordance with the present invention.

Rotatable member 108 forms an interior cavity 302 which is open at both ends to receive guide 110 and form a passage for the instrument cable 102. The instrument cable passes through an opening 310 in the first end and opening 312 in a second end of the rotatable member 108. Opening 312 has a diameter equal to or less than the outer diameter of instrument cable 102 such that when rotatable member 108 is rotated, the instrument cable 102 is rotated at its proximal end as well as being rotated at its distal end by distal rotatable member 122. This arrangement spreads torque along the length of instrument cable 102 giving greater control over the rotation of instrument 124 at the distal end of endoscope 100.

In the depicted embodiment, rotatable member 108 is a tube comprising a helical channel 300 recessed into the wall of interior cavity 302. The internal thread 300 is configured to engage with coupling member 114. The pitch of the helical channel is non-locking, so that rotation of the rotatable member 108 is transforms into linear motion of the coupling member 114 on the guide. In other embodiments, the rotatable member 108 may have an inwardly protruding helical track that engages with a cooperating recess on the coupling member.

The actuator 106 and rotatable member 108 assembly comprises fitting portions 304 and 308 which are configured to engage with receiving portions in casing 104, such as flange 210 and opening 204. These portions ensure a good fit between the actuator 106 and rotatable member 108 assembly and casing 104 so that the actuator 106 and rotatable member 108 assembly is free to rotate about its longitudinal axis within the casing 104, but other movement, such as axial or lateral movement, is restricted. In the depicted embodiment, fitting portions 304 and 308 are shown as cylindrical sections having a reduced diameter, but other methods of mounting the actuator 106 and rotatable member 108 assembly may be considered.

Actuator 106 comprises a number of grooves and/or ridges 306 on its outer surface, as shown in FIG. 3B. These ridges 306 are configured to protrude through windows 200 in casing 104 to allow a user, such as a surgeon or assistant, to rotate actuator 106. The ridges 306 provide grip and are engageable by, for example, the thumb or finger of a user when they are holding the endoscope 100.

Figure 4A:
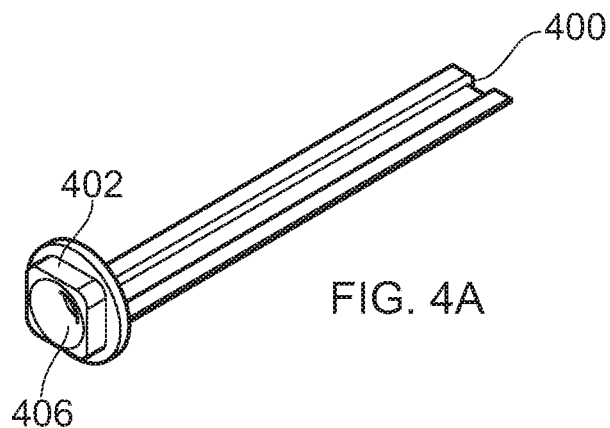
FIGS. 4A, 4B, and 4C show a perspective view, side view, and end view of a guide suitable for use in the rotation mechanism shown in FIG. 1.
Figure 4B:
Figure 4C:

FIGS. 4A, 4B and 4C show a perspective view (FIG. 4A), side view (FIG. 4B) and end view (FIG. 4C) of guide 110. The guide 110 sits inside rotatable member 108 and provides a track for the coupling member 114 to move along when engaged by helical thread 300.

Guide 110 comprises a track 400 which runs from a first end to a second end of the guide 110. Track 400 has a central groove along its length which is configured to receive a protrusion on coupling member 114 and so restrict movement of the coupling member 114 to an axial direction between the first and second ends of guide 110. The track 400 should be narrower than the diameter of the interior cavity 302 of rotatable member 108 so the guide 110 is able to sit inside the interior cavity 302, held by the cavity walls to prevent lateral movement, in such a way that the helical thread 300 can engage coupling member 114.

The first end of the guide 110 is shaped to fit a flange 210 of the casing 104. For example, in FIG. 4A, the first end has a square shape 402 such that when it is fitted with the flange 210, the fit between the square shape 402 and the flange 210 prevents rotation of guide 110 about its longitudinal axis. The guide 110 is resistant to torsion so that the track 400 is not deformed by coupling member 114 due to rotation of rotatable member 108; this helps to ensure that follower 114 moves only in an axial direction.

The guide 110 is also provided with a rim 404 at its first end which is configured to fit between the actuator 106 and an inner surface of the casing 104 proximate the first end of the casing 104, such that when the two halves of the casing 104 are brought together the casing and actuator 106 clamp the rim 404, holding the guide 110 in place.

The first end of guide 110 further comprises a hole 406 for the instrument cable 102 to pass through.

Figure 5A:
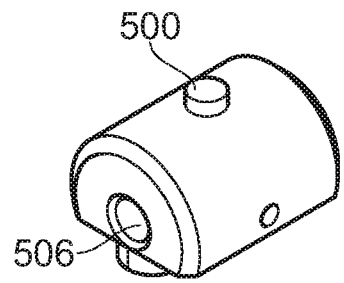
FIGS. 5A, 5B, and 5C show a perspective view, side view, and end view, respectively, of the coupling member shown in FIG. 1.
Figure 5C:
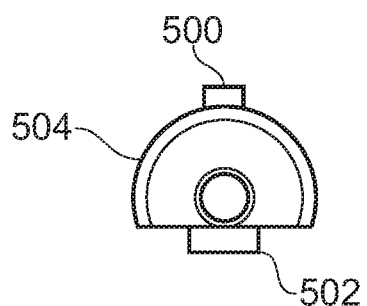
Figure 5B:
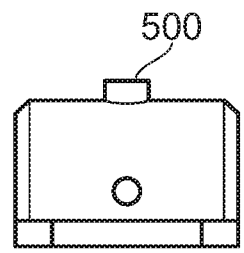

FIGS. 5A, 5B and 5C show a perspective view (FIG. 5A), side view (FIG. 5B) and end view (FIG. 5C) of coupling member 114. The coupling member 114 is positioned on guide 110 in the interior cavity 302 of rotatable member 108, and is configured to engage with helical thread 300 such that it is moved in an axial direction along guide 110 by rotation of the helical thread 300.

The top edge of coupling member 114 comprises a pin 500 which is configured to fit into the recessed helical thread 300. In the pictured embodiment, pin 500 is a cylinder protruding from the top surface of the coupling member 114; this shape ensures a good fit with the recessed helical thread 300 at all times, and has low friction to ensure smooth following movement with the helical thread 300. Other than pin 500, the top edge of coupling member 114 has a curved surface 504 which matches with the surface of interior cavity 302. When pin 500 is engaged with the helical thread 300, curved surface 504 abuts the surface of the interior cavity 302. This arrangement helps to ensure that pin 500 is located within the recessed helical thread 300 at all times during use.

The bottom edge of coupling member 114 presents a flat surface to track 400 of the guide 100. The bottom edge also comprises a protrusion 502 which is configured to fit the groove of track 400 such that movement of the follower on the guide 110 is constrained to an axial direction. A close fit between the surfaces of the interior cavity 302 and guide 110, and surfaces of coupling member 114 helps ensure smooth axial movement of coupling member 114 along guide 108 when rotatable member 108 is rotated by a user, and also reduces rotational or lateral movement.

The coupling member 114 further comprises a longitudinal passage 506 from a first side to a second side of the coupling member 114 for the instrument cable 102 to pass through.

FIG. 6 shows a perspective view of distal rotatable member 122. The distal rotatable member 122 is a laser cut sleeve comprising a helical strip cut at an angle of 80° wide from the centre of the helix. The rotatable member 122 is fitted over the instrument cable 102 and fixed to the cable by end clips 600 which grip instrument cable 102. In the pictured embodiment, the clips 600 are 3 mm long with an interior diameter of 2.54 mm, an exterior diameter of 3.048 mm, and a wall thickness of 0.254 mm.

The distal rotatable member 122 comprises a helical strip with three full rotations and a total length (including end clips 600) of 118.5 mm. Each rotation is clockwise from a first end to a second end (left to right as seen in FIG. 6) with a pitch of 37.5 mm.

FIGS. 7A and 7B show an end view (FIG. 7A) and magnified view (FIG. 7B) of the distal coupling member 120. The distal coupling member 120 is attached, for example with adhesive, to the inner surface of the follower 116.

Distal coupling member 120 is configured to engage with the distal rotatable member 122. In this respect, distal coupling member 120 takes the form of a tube or ring element having a helical cut-out section 700, which is cut at an angle of 85° wide from the centre of the tube with a pitch length of 37.5 mm, the helix running in the clockwise direction to match the helix of the distal rotatable member 122. In the pictured embodiment, the distal coupling member 120 has length of 8 mm, an outer diameter of 3.2 mm, an inner diameter of 2.692 mm and a wall thickness of 0.254 mm. These measurements ensure that the distal coupling member 120 is able to freely slide along instrument cable 102, with minimal friction between distal coupling member 120 and instrument cable 102, in response to axial movement of the follower 116, and engage with distal rotatable member 122 so as to rotate the instrument cable 102. These measurements will vary depending on the dimensions of the instrument cable 102 and distal rotatable member 122. For example, the pitch of cut-out 700 should match the pitch of the helical strip of distal rotatable member 122, and the wall thickness of the distal follower 120 should be chosen according to the diameter of the instrument cable 102.

Surface portion 702 of the distal coupling member 120 may have adhesive applied to it in order to attach distal coupling member 120 to the inside surface of the follower 116.

Cut-out section 700 has rounded edges 704, each corner having a 0.8 mm radius curve. This helps to ensure smooth movement of the distal coupling member 120 along distal rotatable member 122, reducing friction between the parts.

Figure 8:
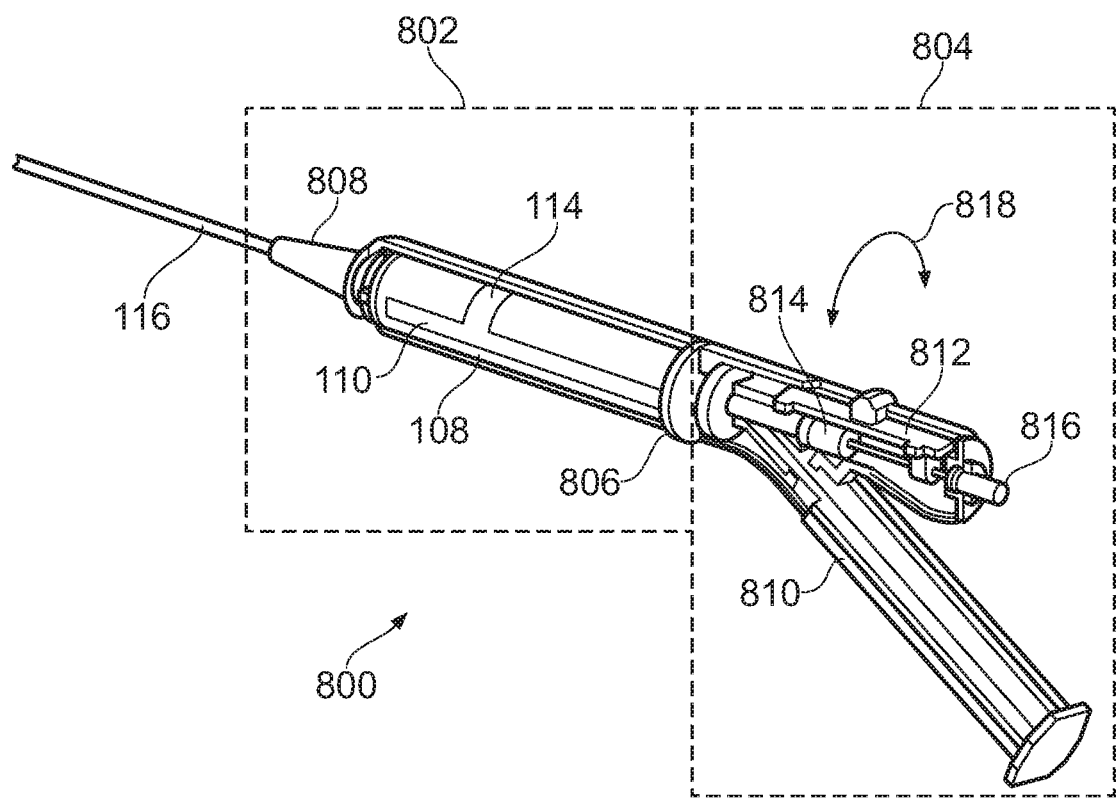
FIG. 8 shows a section view of a handle of an endoscope according to an alternative embodiment of the present invention.

FIG. 8 shows a section view of a handle 800 of an endoscope according to an alternative embodiment of the present invention. Parts equivalent to those described above have been given similar reference numerals for ease of identification.

Handle 800 is formed from a first section 802 and a second section 804. The first section comprises an outer casing which houses a rotatable member 108, coupling member 114 and a guide 110, wherein the coupling member 114 and guide 110 are disposed within the rotatable member 108. The rotation mechanism is actuated by causing relative rotation between the first section 802 and second section 804. The rotatable member 108 may be connected to the second section 804 by a connector 806, whereas the guide 110 may be fixed relative to the first section 802. The connector 806 transmits relative rotation of second section 804 to the rotatable member 108, and comprises a flange to create a seal between the first section 802 and second section 804 of handle 800 which is not broken by relative rotation of the two sections. Rotation of the rotatable member 108 results in rotation of a surgical instrument 124 at the distal end of the endoscope (not shown) as described above with respect to FIGS. 1-7.

Handle 800 comprises strain relief 808 which is configured to relieve strain/stress on follower 116 and the instrument cable 102 within the follower 116 and so avoid damaging these components. Handle 800 further comprises a saline injection port 810 for injecting saline through a saline channel to a needle disposed at the distal end of the endoscope (not shown). The needle is part of the surgical instrument at the end of the endoscope, and so is rotated with the surgical instrument 124 by rotation of the second section 804 of the handle 800. A needle push 812 is configured to push the needle out of a recess within the surgical instrument 124 when the needle push 812 is moved from a first position to a second position by sliding the needle push 812 towards the first section 802 of the handle 800. A seal 814 is provided to prevent saline flowing from the instrument channel into handle 800.

Instrument cable 102, may include a coaxial transmission line configured to transmit radiofrequency and/or microwave frequency energy through the assembly to a surgical instrument 124, for example an electrosurgical instrument capable of delivering radiofrequency (RF) energy for cutting tissue and/or microwave frequency energy for haemostasis (i.e. promoting blood coagulation). A QMA connector 816 is therefore provided at the rear of handle 800 to connect instrument cable 102 to a suitable radiofrequency or microwave frequency energy source.

Figure 9:
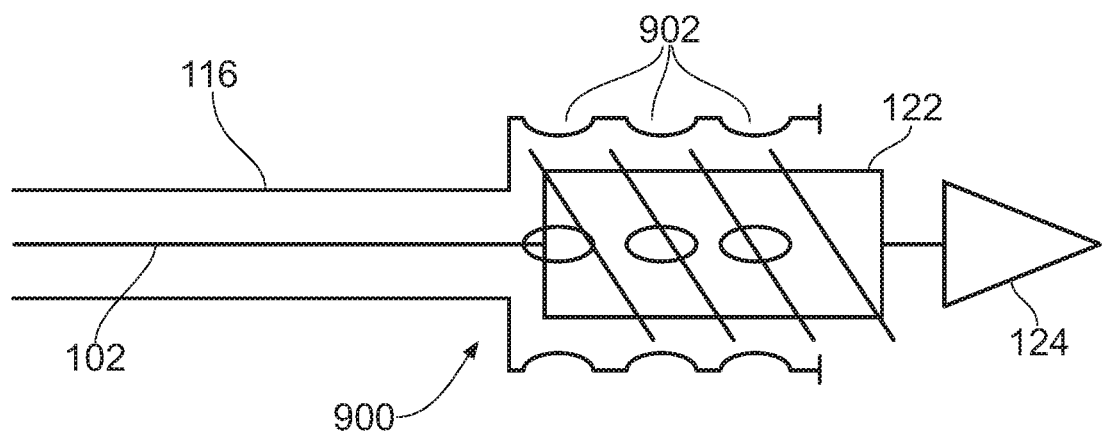
FIG. 9 shows a section view of the distal end of an endoscope in an alternative embodiment of the present invention.

FIG. 9 shows a section view of the distal end of rotation mechanism in an alternative embodiment of the invention. Parts equivalent to those described above have been given similar reference numerals for ease of identification. Due to the addition of distal rotatable member 122 and other components in the instrument channel at the distal end thereof, suction of fluid through the instrument channel and away from the distal end may be more difficult.

To improve suction, follower 116 may have a distal section 900 with an increased diameter. This distal section may be located around distal rotatable member 122 as shown in FIG. 9. To increase fluid flow through the instrument channel, distal section 900 is provided with a plurality of holes 902 through the follower 116 and into the instrument channel. Fluid can therefore more easily enter the instrument channel to be moved away from the distal end of endoscope 100 by suction. The distal coupling member 120 may be attached to the inside of distal section 902 such that it engages distal rotatable member 122, but is omitted from FIG. 9 for clarity.

The invention claimed is:

1. An instrument rotation mechanism for a surgical scoping device, the instrument rotation mechanism comprising:
    a housing mountable at a proximal end of an instrument channel of the surgical scoping device;
    a proximal actuator mounted to rotate relative to the housing about a longitudinal axis of the instrument channel;
    an elongate force transfer element configured to be slidably mounted within and to extend along the instrument channel of the surgical scoping device;
    a proximal coupler operably engaged with the proximal actuator and elongate force transfer element to transform rotational movement of the proximal actuator relative to the housing about the longitudinal axis of the instrument channel into linear movement of the elongate force transfer element relative to the instrument channel along the longitudinal axis of the instrument channel;
    a distal end effector that is securable to a distal portion of a surgical instrument mounted in the instrument channel; and
    a distal coupler operably engaged with the distal end effector and elongate force transfer element to transform linear movement of the elongate force transfer element relative to the instrument channel along the longitudinal axis of the instrument channel into rotational movement of the distal end effector about the longitudinal axis of the instrument channel and relative to the instrument channel.

2. An instrument rotation mechanism according to claim 1, wherein the proximal coupler is slidably mounted in the housing.

3. An instrument rotation mechanism according to claim 1, wherein the housing includes a rotation constraining element arranged to prevent the elongate force transfer element from rotating relative to the housing.

4. An instrument rotation mechanism according to claim 3, wherein the rotation constraining element is arranged to engage the proximal coupler to prevent it from rotating relative to the housing.

5. An instrument rotation mechanism according to claim 4, wherein the rotation constraining element defines a linear sliding track for the proximal coupler.

6. An instrument rotation mechanism according to claim 1, wherein the proximal coupler and proximal actuator are operably connected via a non-locking thread-type engagement.

7. An instrument rotation mechanism according to claim 1, wherein the proximal actuator comprises a helical formation and the proximal coupler comprises an engagement element mounted on and movable along the helical formation.

8. An instrument rotation mechanism according to claim 7, wherein the helical formation is a recessed track and the engagement element is a pin that sits in the recessed track.

9. An instrument rotation mechanism according to claim 1, wherein the distal coupler and distal end effector are operably connected via a non-locking thread-type engagement.

10. An instrument rotation mechanism according to claim 1, wherein the distal end effector comprises a helical formation and the distal coupler comprises an engagement element mounted on and movable along the helical formation.

11. An instrument rotation mechanism according to claim 10, wherein the helical formation is a helical sleeve mounted around the distal portion of the surgical instrument, and the engagement element comprises a ring having a helical portion that cooperate with the helical sleeve.

12. An instrument rotation mechanism according to claim 1, wherein:
    the proximal actuator comprises a first helical formation and the proximal coupler comprises a first engagement element mounted on and movable along the first helical formation,
    the distal end effector comprises a second helical formation and the distal coupler comprises a second engagement element mounted on and movable along the second helical formation, and
    a pitch of the first helical formation is greater than a pitch of the second helical formation.

13. An instrument rotation mechanism according to claim 12, wherein the pitch of the first helical formation is equal to or greater than 1.5 times the pitch of the second helical formation.

14. An instrument rotation mechanism according to claim 1, comprising an instrument cable that extends through the instrument channel for connection to the surgical instrument, wherein the proximal actuator is secured to a proximal portion of the instrument cable.

15. An instrument rotation mechanism according to claim 14, wherein the distal end effector is secured to a distal portion of the instrument cable.

16. An instrument rotation mechanism according to claim 1, wherein the elongate force transfer element comprise a proximal portion and a distal portion, and wherein the instrument rotation mechanism further comprises;
    an intermediate rotatable member located between the proximal portion and distal portion of the elongate force transfer element,
    a proximal intermediate coupler operably engaged with the intermediate rotatable member and the proximal portion of the elongate force transfer element to transform linear movement of the proximal portion of the elongate force transfer element relative to the instrument channel into rotational movement of the intermediate rotatable member relative to the instrument channel, and a distal intermediate coupler operably engaged with the intermediate rotatable member and the distal portion of the elongate force transfer element to transform rotational movement of the intermediate rotatable member relative to the instrument channel into linear movement of the distal portion of the elongate force transfer element relative to the instrument channel.

17. An instrument rotation mechanism according to claim 16, wherein the intermediate rotatable member comprises a helical sleeve and the proximal intermediate coupler and the distal intermediate coupler each comprise a ring having a helical cut-out section configured to cooperate with the helical sleeve.

18. An instrument rotation mechanism according to claim 1, wherein the housing is part of a handle for operating the surgical scoping device.

19. An instrument rotation mechanism according to claim 1, wherein the elongate force transfer element comprises a sleeve having a longitudinal passage therethrough for conveying an instrument cable along the instrument channel.

20. An instrument rotation mechanism according to claim 19, wherein the sleeve is porous at its distal end to facilitate fluid flow through the instrument channel.

21. An instrument rotation mechanism according to claim 20, wherein the sleeve comprises a plurality of holes at its distal end.

22. An instrument rotation mechanism according to claim 1, wherein the elongate force transfer element is any of:
   a plastic extruded catheter,
   a laser cut tube,
   a tube formed of encapsulated braiding.

23. An instrument rotation mechanism according to claim 1, wherein elongate force transfer element is manufactured from PEEK, polyimide, or stainless steel.

* * * * *